United States Patent [19]

Braidwood

[11] Patent Number: 6,160,023
[45] Date of Patent: Dec. 12, 2000

[54] USE OF BRONOPOL FOR THE TREATMENT OF DISEASES IN FISH

[75] Inventor: Julian Charles Braidwood, Cumbria, United Kingdom

[73] Assignee: Vericore Limited, Lancashire, United Kingdom

[21] Appl. No.: 09/230,775

[22] PCT Filed: Jul. 29, 1997

[86] PCT No.: PCT/GB97/02042

§ 371 Date: Feb. 1, 1999

§ 102(e) Date: Feb. 1, 1999

[87] PCT Pub. No.: WO98/05311

PCT Pub. Date: Feb. 12, 1998

[30] Foreign Application Priority Data

Aug. 1, 1996 [GB] United Kingdom .................. 9616139

[51] Int. Cl.⁷ ................................................ A61K 31/045
[52] U.S. Cl. ............................................................ 514/727
[58] Field of Search .................... 514/361, 727; 435/226, 6

[56] References Cited

U.S. PATENT DOCUMENTS 3,880,827  4/1975  Eble et al. ......................... 536/16.8
5,457,025  10/1995  Collins et al. ........................... 435/6
5,834,290  11/1998  Egelrud et al. ....................... 435/226
5,942,528  8/1999  Heil et al. ............................. 514/361

FOREIGN PATENT DOCUMENTS 38833    7/1986  Hungary .
2014848  9/1979  United Kingdom .
2263063  7/1993  United Kingdom .

Primary Examiner—William R. A. Jarvis
Assistant Examiner—Vickie Kim
Attorney, Agent, or Firm—Dann Dorfman Herrell and Skillman, P.C.

[57] ABSTRACT

The invention relates to the use of bronopol (bromo-2-nitropropane-1,3-diol), in the treatment of various diseases of aquatic organisms, particularly salmonid fish and their eggs. The diseases which can be treated include thgose caused by fungal infections (such as *Saprolegnia parasitica*); protozoan infections, whether flagellate (such as *Ichthyobodo necatrix*) or ciliate (such as *Icthyophthirius multifiliis*); bacteria (such as *Flavobacterium branchiophilum*); and myxobacteria (such as *Cytophaga psychrophila*). Also disclosed is a method of disinfecting fish tanks and/or equipment, using a solution of bronopol.

14 Claims, 5 Drawing Sheets

USE OF BRONOPOL FOR THE TREATMENT OF DISEASES IN FISH

CONTINUING DATA

This application is a 371 of PCT/GB97/02042 filed on Jul. 29, 1997.

This invention relates Go the treatment of fungal infections (especially *Saprolegnia parasitica*) of fish, particularly, but not exclusively, trout, salmon, salmonids in general, and their eggs. The invention also provides treatments of other fish diseases such as bacterial infections (for example bacterial gill disease—*Flavobacterium branchiophilum* and *Cytophaga psychrophila*), protozoan infections such as ciliates (for example *Ichthyophthirius multifiliis*) and flagellates (for example *Ichthyobodo necatrix*).

*Saprolegnia parasitica* is a rapidly spreading and fatal fungal parasite affecting both fish and fish eggs. It is conventionally treated with malachite green (diaminotriphenylmethane), but though this treatment is highly effective, the use of malachite green carries with it a number of potential problems: the compound has been suggested as a possible carcinogen and teratogen, though these effects are as yet unproven; being a strong dye, it tends to discolour water, and can under certain conditions cause staining of fish which have been treated; it has a relatively long withholding period, so that significant residues can be present in treated fish when they are harvested and sold for consumption; and the compound is not licensed as a veterinary medicament, and is actually banned from use in U.S. Federal hatcheries. The article by D. J. Alderman in Journal of Fish Diseases 8 (1985) 289–298 gives a review of the use of malachite green in treating fish diseases, and discusses some of the problems associated therewith.

One currently available alternative to malachite green is formalin, which is the substance which is now used in US Federal hatcheries. However, due to the irritancy of this substance, it can only be used under strictly controlled conditions. There is therefore a need for an improved treatment for fungal and other diseases of fish, particularly one which combines high efficacy with low toxicity. Many attempts to identify new treatments have been made in the past and the results of the screening of 40 potential alternative substances are set out in the article by D. J. Alderman appearing at Journal of Fish Diseases 5 (1982) 113–123, which also sets down standard protocols for the testing of candidate treatments. However, despite this and other work (such as that described in the article by T. A. Bailey appearing at Aquaculture 38 (1984) 97–104), the applicants are not aware of any suitable alternative treatments to malachite green and formalin having reached the marketplace.

It has now been found that bronopol (2-bromo-2-nitropropane-1,3-diol) has good activity at relatively low concentrations against *Saprolegnia parasitica*, and is safe to use. Bronopol is a known compound, and is used in concentrations of between 0.01 and 0.2% as an antimicrobial preservative and antiseptic in topical pharmaceutical formulations, cosmetics, and toiletries. It is stated however in "Handbook of Pharmaceutical Excipients" published by The Pharmaceutical Press (1994) that one of bronopol's major disadvantages is its relatively poor activity against yeasts and moulds. It is therefore surprising that bronopol is effective at relatively low concentrations against Saprolegnia.

As will be described in more detail below, bronopol has been shown to be effective against *Saprolegnia parasitic-* *a*infection in salmon, trout and trout eggs. It is envisaged however that the treatment will be effective against the same infection in other salmonid species, and indeed in other fish (for example ornamental or pet fish), fish eggs and other aquatic creatures (such as shrimps or prawns) in general. It is expected that there will also be efficacy against other fungal infections. Furthermore, as bronopol has been shown in the trials described below to prevent or slow the spread of infection, it may also be used as a prophylactic.

Bronopol is a commercial product available from a number of sources. It may be manufactured by reacting nitromethane with paraformaldehyde in an alkaline environment, followed by bromination. It is also known that some compounds (such as 5-bromo-5-nitro-1,3-dioxane) break down to release bronopol, and the invention therefore also extends to the use of such compounds in the place of bronopol.

Thus, the invention provides, in one aspect, the use of bronopol, or a compound releasing bronopol in use, in the manufacture of a medicament for the treatment or prophylaxis of fungal infections in fish, fish eggs or other aquatic organisms. More specifically, the invention relates to the use of bronopol in the treatment and/or prophylaxis of *Saprolegnia parasitica*. One particular use of the invention will be in the treatment of salmonid fish and their eggs, particularly trout and salmon.

The invention also extends to a method of treating fish, fish eggs or other aquatic organisms suffering from fungal infection by administering bronopol, or a compound releasing bronopol in use, in a treatment bath in a pharmaceutically effective amount. Preferably the method includes the step of halting water flow through the bath while the treatment is administered, preferably for a period of not less than 30 minutes.

Preferably, the concentration of bronopol in the treatment bath is in the range of 1 mg.l$^{-1}$ (ppm) to 1000 mg.l$^{-1}$ more preferably 5 mg.l$^{-1}$ to 200 mg.l$^{-1}$, and ideally 10 mg.l$^{-1}$ to 100 mg.l$^{-1}$. Bronopol is a solid crystalline substance, and may conveniently be prepared as a solution in a polar solvent, such as water or Dowanol (dipropylene glycol monoethylether).

Figure 1:
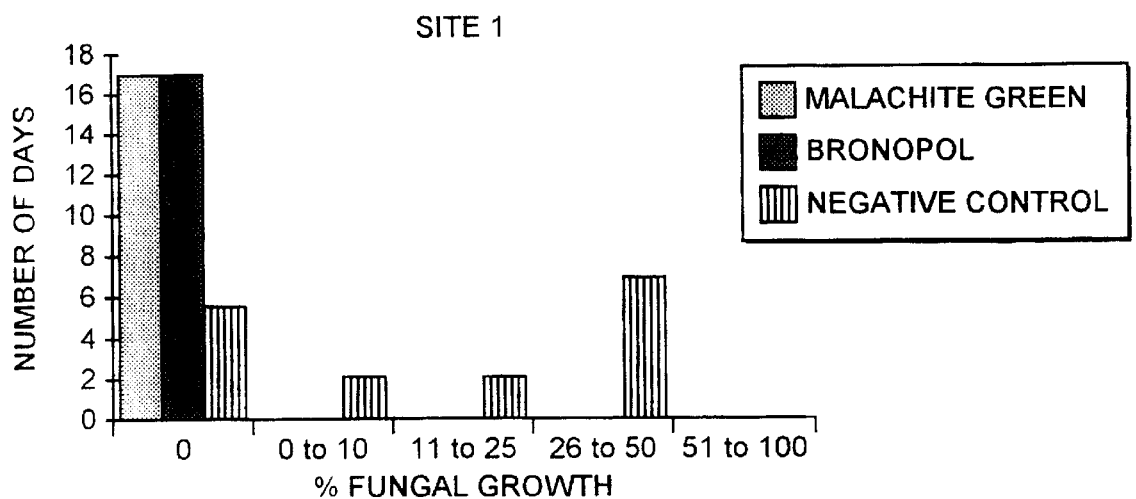
FIGS. 1–3 are graphical representations of the results of testing conducted to determine the in vivo efficacy of bronopol against *Saprolegnia parasitica* infection in trout eggs.

Trial 1 (below) was conducted in mildly alkaline conditions (approximately pH 7.4 to 7.5) and it is possible that these conditions are favourable for the anti-fungal activity demonstrated by bronopol.

During the trials, bronopol was also tested against various other fish diseases, and was found to be effective against *Ichthyobodo necatrix*, which is an ectoparasite flagellate protozoan, *Flavobacterium branchiophilum* (the causative organism of bacterial gill disease), and *Cytophaga psychrophila*, which is a myxobacterium and the causative organism of Rainbow Trout Syndrome, Coldwater disease, Saddleback and Peduncle disease in salmonid fish. The activity against Cytophaga indicates possible efficacy against myxobacteria in general, and the activity against Ichthyobodo suggests efficacy against flagellates in general, as well as ciliate protozoans such as *Ichthyophthirius multifiliis*.

Thus, in a further aspect the invention extends to the use of bronopol, or a compound releasing bronopol in use, in the manufacture of a medicament for the treatment or prophylaxis of a protozoan infection, such as a flagellate (for example *Ichthyobodo necatrix*) or a ciliate (such as *Ichthyophthirius multifiliis*) in fish or other aquatic organisms, particularly salmonid fish, and especially trout.

In an alternative aspect, the invention extends to the use of bronopol, or a compound releasing bronopol in use, in the manufacture of a medicament for the treatment or prophylaxis of bacterial gill disease (for example *Flavobacterium branchiophilum*) in fish or other aquatic organisms, particularly salmonid fish, and especially trout.

The invention also encompasses a method of treating such protozoan or flavobacterium infections in fish or other aquatic organisms by administering bronopol, or a compound releasing bronopol in use, in a treatment bath in a pharmaceutically effective amount. Preferably, the bronopol is administered in a concentration of between 1 and 500 mg.l$^{-1}$, more preferably between 10 and 100 mg.l$^{-1}$.

The main practical use of the activity against Cytophaga is likely to be in the disinfection of tanks and equipment and the invention therefore encompasses a method of disinfecting fish tanks and/or instruments for use in the husbandry of fish, the method comprising the step of exposing the tank/equipment to a solution containing bronopol, or a compound releasing bronopol in use. Preferably, the bronopol is present in a concentration of between approximately 1 and 2000 mg.l$^{-1}$, more preferably 5 to 1000 mg.l$^{-1}$. The exposure time is preferably between 2 and 40 mins.

It is possible that bronopol may also be effective in treating fish suffering from myxobacterial infection, and the invention therefore also extends to the use of bronopol, or a compound releasing bronopol in use, in the manufacture of a medicament for the treatment or prophylaxis of myxobacterial infections (particularly *Cytophaga psychrophila*) of fish or other aquatic organisms, particularly salmonid fish, and especially trout.

The invention is hereinafter described in more detail by way of example only, with reference to the following experimental trials:

Trial 1

In Vitro Efficacy of Bronopol Against *Saprolegnia parasitica*

This trial was carried out using the procedures described in Journal of Fish Diseases (1982) 5, 113–123, cited above.
Preparation of Inocula A culture of *Saprolegnia parasitica* was maintained at 16° C. on river water, glucose, yeast extract agar (RGY), consisting of yeast extract (1 g), D(+)glucose (5 g), and agar (12 g) in 1 l river water. Plates of RGY were seeded with the test organism and incubated at 25° C. until growth just covered the full diameter of the dish (approximately 72 hours). Discs were cut from the outer 10 mm of the culture, using a 4-mm diameter punch (adapted from a gel chromatography well punch by welding-on a handle) and then used as standard inocula for testing.

Test 1A

Method

Bronopol was tested for activity against the *Saprolegnia parasitica* cultures at different concentrations ranging from 50mg.l$^{-1}$ to 100 mg.l$^{-1}$, using Protocol II of the aforementioned J. Fish Diseases article, as follows. Polycarbonate filter membranes of 0.2-$\mu$m porosity and 25-mm diameter (Nuclepore; Sterlin) were sterilized by autoclaving and then placed on the surface of RGY plates (7 per 90-mm petri-dish). A standard 4-mm disc inoculum was then placed, inverted, at the centre of the filter. The dishes containing the filters were then incubated until the resulting mycelial mat had almost reached the edge of the filters. The original inocula were then clipped off (as far as practical) using hot forceps tips to avoid disturbing the loosely adherent mycelial mat. The mycelial mats together with their supporting filters were lifted off the agar surface on the filters, transferred to empty, sterile, petri-dishes and completely submerged in the bronopol solution at selected concentrations. At the end of the 1 hour exposure period the bronopol solution was removed by aspiration and replaced by two washes of sterile river water (for 5 and 30 min, respectively) before the mycelial mat and filter were transferred, filter uppermost, to the surface of a fresh RGY plate. After incubation at 16° C. for 24 h, any new growth beyond the edge of the filter was measured at four points around the filter, at 90° intervals.

The experiment was performed using six separate culture samples at each concentration of bronopol, and was repeated using malachite green in place of bronopol. A negative control test using no active agent was also performed. The results are set out in the table below:

TABLE 1A

| Conc | Time | BRONOPOL | | | | | | MALACHITE GREEN | | | | | |
|---|---|---|---|---|---|---|---|---|---|---|---|---|---|
| mg · l$^{-1}$ | (min) | 1 | 2 | 3 | 4 | 5 | 6 | 1 | 2 | 3 | 4 | 5 | 6 |
| 1000 | 10 | 0 | 0 | 0 | 0 | 0 | 0 | 0 | 0 | 0 | 0 | 0 | 0 |
| 500 | 10 | 0 | 0 | 0 | 0 | 0 | 0 | 0 | 0 | 0 | 0 | 0 | 0 |
| 100 | 10 | 3 | 3 | 2 | 2 | 1 | 2 | 0 | 0 | 0 | 0 | 0 | 0 |
| 50 | 10 | 3 | 3 | 3 | 3 | 2 | 2 | 0 | 0 | 0 | 0 | 0 | 0 |
| 50 | 5 | 5 | 2 | 2 | 3 | 3 | 4 | 0 | 0 | 0 | 0 | 0 | 0 |
| 10 | 10 | 6 | 7 | 7 | 6 | 7 | 6 | 0 | 0 | 0 | 0 | 0 | 0 |
| 10 | 5 | 7 | 7 | 7 | 6 | 8 | 8 | 0 | 0 | 0 | 0 | 0 | 0 |
| Control | 10 | 7 | 7 | 7 | 6 | 7 | 7 | | | | | | |

Radial growth in mm at 24 h after exposure to bath of test concentration

Discussion

In this test naked fungal hyphae are exposed to bronopol, which is shown to have an inhibitory effect as low as 50 ppm for 5 minutes against subsequent vegetative growth. Ten minutes' exposure at 500 ppm prevents all subsequent vegetative growth with this test method.

Test 1B

Method

In this test, bronopol was tested for efficacy against *Saprolegnia parasitica* using the more demanding Protocol III of the aforementioned J. Fish Diseases article, the method being as follows:

Four disc inocula were placed in each compartment of a sterile replidish (25 compartments in five rows; Sterilin).

Five different test concentrations applied for five different exposure times could thus be carried out in quadruplicate in one dish. The test concentrations were added aseptically in volumes of 2.5 ml to each compartment for the standard exposure times, which were 5, 10, 20, 40 and 80 mins. At the end of the individual exposure times, the test solutions were removed from the compartments by aspiration. Each set of discs was then washed in situ in two changes of sterile river water (for 5 and 30 mins, respectively) and then incubated in a further 2.5 ml of sterile river water, in situ, for 72 h at 16° C. Subsequently, the discs were examined under a stereomicroscope, using transmitted dark-ground illumination, and scored for presence or absence of new growth on the agar disc surface. In all cases of doubt, particularly at the borderline between growth and no growth, discs were then transferred to RGY for a further 72 h at 16° C. to determine accurately the viability of the mycelium within the disc. The test was repeated, substituting malachite green oxalate for bronopol.

The results were expressed both in terms of effect on zoosporulation and in terms of effect on vegetative growth, and are set out in the tables below:

TABLE 1B(i)

Bronopol - Effect on zoosporulation (percentage inhibition)

| 100% | 100% | 0 | 0 | 0 | 80 | T |
| 100% | 100% | 0 | 0 | 0 | 40 | i |
| 100% | 100% | 0 | 0 | 0 | 20 | m |
| 100% | 100% | 0 | 0 | 0 | 10 | e |
| 100% | 100% | 0 | 0 | 0 | 5 | (min) |
| 1000 | 100 | 10 | 1 | 0 | | |

Concentration (mg. $l^{-1}$)

TABLE 1B(ii)

Malachite green oxalate - Effect on zoosporulation (percentage inhibition)

| 100% | 100% | 100% | 100% | 0 | 80 | T |
| 100% | 100% | 100% | 100% | 0 | 40 | i |
| 100% | 100% | 100% | 100% | 0 | 20 | m |
| 100% | 100% | 100% | 40–50% | 0 | 10 | e |
| 100% | 100% | 100% | 40–50% | 0 | 5 | (min) |
| 1000 | 100 | 10 | 1 | 0 | | |

Concentration (mg. $l^{-1}$)

TABLE 1B(iii)

Bronopol - Effect on vegetative growth (percentage inhibition)

| 100% | 10–20 | 0 | 0 | 0 | 80 | T |
| 100% | 0 | 0 | 0 | 0 | 40 | i |
| 100% | 0 | 0 | 0 | 0 | 20 | m |
| 10–20% | 0 | 0 | 0 | 0 | 10 | e |
| 10–20% | 0 | 0 | 0 | 0 | 5 | (min) |
| 1000 | 100 | 10 | 1 | 0 | | |

Concentration (mg. $l^{-1}$)

TABLE 1B(iv)

Malachite green oxalate - Effect on vegetative growth (percentage inhibition)

| 100% | 100% | 100% | 0 | 0 | 80 | T |
| 100% | 100% | 100% | 0 | 0 | 40 | i |

TABLE 1B(iv)-continued

Malachite green oxalate - Effect on vegetative growth (percentage inhibition)

| 100% | 100% | 100% | 0 | 0 | 20 | m |
| 100% | 100% | 100% | 0 | 0 | 10 | e |
| 100% | 100% | 100% | 0 | 0 | 5 | (min) |
| 1000 | 100% | 10 | 1 | 0 | | |

Concentration (mg. $l^{-1}$)

Discussion

Bronopol has a marked effect on immediate zoosporulation with exposures as little as 5 minutes at concentrations of 100 ppm or (possibly) less. This test uses an agar plug method, in which the agar containing the mycelium obviously offers protection to the hyphae, but bronopol still penetrates and a 20 minute 1,000 ppm exposure prevents all subsequent growth, and this concentration also has a significant effect in as short as 5 minutes. Furthermore, the lower 100 ppm exposure for 80 minutes also appears to have some inhibitory effect.

Trial 2

In Vivo Efficacy of Bronopol Against *Saprolegnia parasitica* Infection in Trout Eggs Approximately 913,000 rainbow trout eggs were used in this trial, which was split between three farm sites. In each case, the eggs were carefully measured into incubators or trays and very gently immersed in water at an even temperature, after removing any faeces, blood or white (dead) eggs. The eggs were monitored until they reached the eyed stage, and were then shocked by dropping into water from a height of approximately 0.5 m. The purpose of shocking is to kill any weak or infertile eggs, which turn white due to the rupture of the inner membrane. Dead eggs were removed and counted. The trial was continued until the eggs hatched, at which time dead eggs were again removed and counted. Throughout the trial the degree of fungal infection (attributed to Saprolegnia) was monitored.

The first farm site (Site 1) was run on ground water and the eggs were maintained in a trough and tray system from stripping to hatching. Incubator volumes were 101 l, with a water exchange rate of 40 $l.min^{-1}$ (the time for water exchange being 2.5 min).

Site 2 was also run on ground water. From stripping to shocking the eggs were kept in vertical incubators, of 20 l volume. The water exchange rate was 13.6 $l.min^{-1}$ and the time for water exchange 1.5 min. From shocking to hatching the eggs were kept in a trough and tray system, the incubator volumes being 145 l and the water exchange rate 27 $l.min^{-1}$ (the water exchange time being 5.4 min). The eggs at Site 2 were divided into 3 batches which were tested separately and at different times.

Site 3 was run on river water, and the eggs were maintained in a trough and tray system from stripping to hatching. Incubators were of 190 l in volume, with a water exchange rate of 10 $l.min^{-1}$ and a water exchange time of 19 min.

At each site (and for each batch at Site 2), the eggs were divided into three treatment groups, one receiving bronopol treatment, one receiving malachite green treatment, and one receiving no treatment (to act as a negative control). The number of eggs in each group was as follows:

TABLE 2A

Number of eggs per treatment group

| Site | Bronopol | Malachite Green | Negative Control |
|---|---|---|---|
| 1 | 231,040 | 115,520 | 24,320 |
| 2 | 108,000 | 108,000 | 16 000 |
| 3 | 249,382 | 45,579 | 24,580 |

Bronopol at a concentration of 500 g.l$^{-1}$ was added at the top of the incubators and distributed through the eggs with the incoming water. The water flow was then turned off when the treatment was estimated to be half-way through the trough. A bath lasting 30 minutes was then formed in which the concentration of bronopol was generally in the range of 1 mg.l$^{-1}$ to 50 mg.l$^{-1}$.

Malachite Green was used as a flush treatment. It was administered at the top of the incubator and flushed through the eggs with the incoming water (the water flow was not turned off). This was the usual method on all of the sites. The dosage varied from site to site as follows: Site 1 15 mg.l$^{-1}$; Site 2 40 mg.l$^{-1}$; Site 3 5 mg.l$^{-1}$.

Eggs in both bronopol and malachite green groups were treated every day from stripping to hatching.

Figure 3:
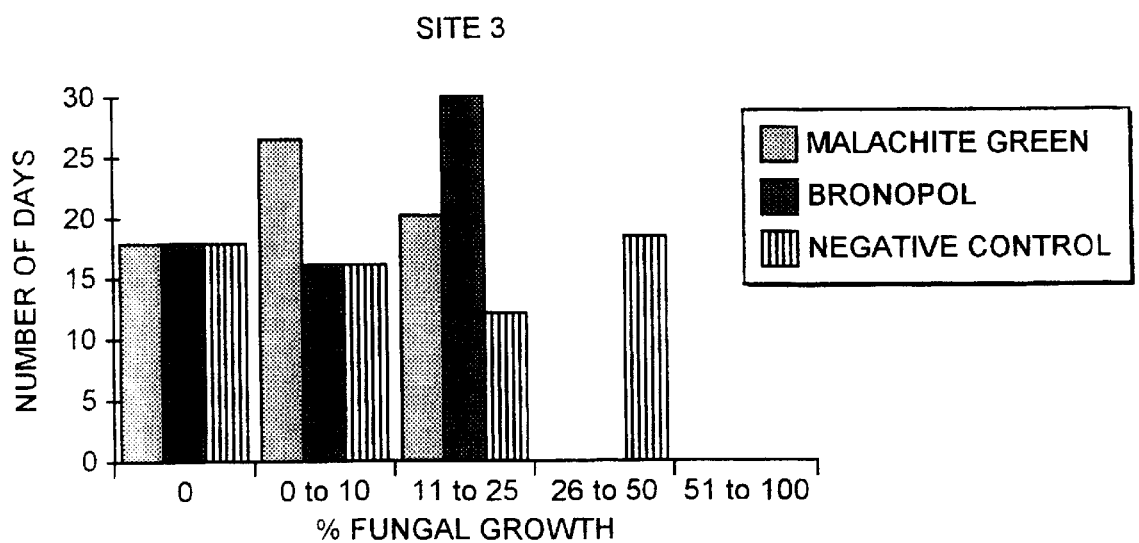
Figure 2:
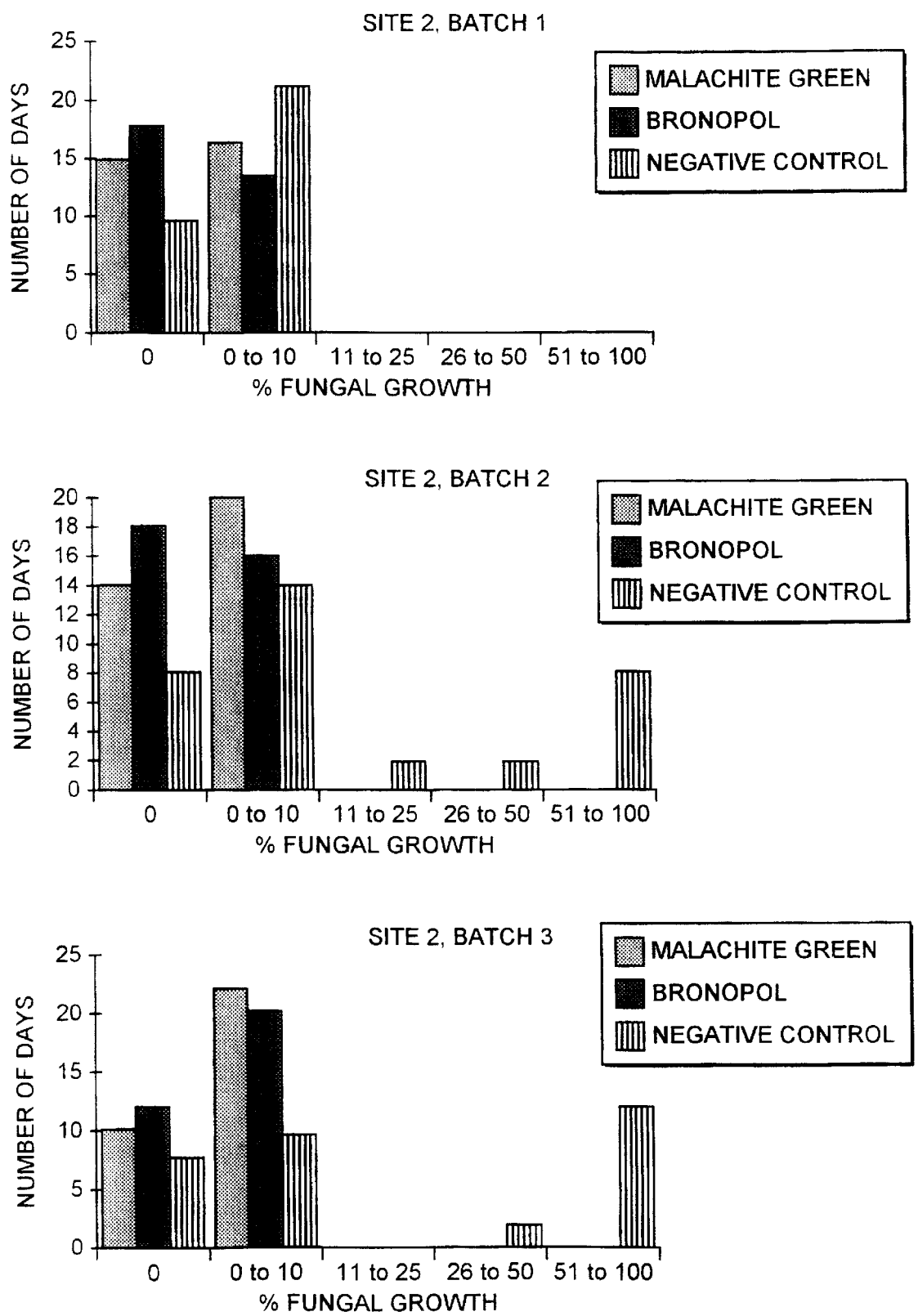

Fungal growth was assessed visually as the percentage of eggs covered with fungal growth, on every second day of the study at Sites 1 and 2, and every day on Site 3. The results are displayed graphically in FIGS. 1 to 3 and are summarised in Table 2B below:

TABLE 2B

Percentage of Treatment days with degree of fungal growth

| Percentage Fungal Growth | Malachite Green | Bronopol | Negative Control |
|---|---|---|---|
| 0% | 41.57% | 46.63% | 28.09% |
| 0% to 10% | 47.19% | 36.52% | 35.39% |
| 11% to 25% | 11.24% | 16.85% | 8.99% |
| 26% to 50% | 0.00% | 0.00% | 16.29% |
| 51% to 100% | 0.00% | 0.00% | 11.24% |

Table 2B shows that bronopol has resulted in no fungal growth for 46.63% of the days that the eggs were treated. This can be compared with 41.57% for Malachite Green and 28.09% when no treatment is applied. Both bronopol and Malachite Green prevented the eggs being covered with more than 25% fungal growth.

Dead eggs were counted and removed at shocking and at hatching and the numbers of dead eggs in each case are set out in Tables 2C to 2K below. Tables 2L & 2M show overall mortalities at shocking and hatching, respectively. (Site 1 did not record mortalities at hatching, hence the lower original value in table 2M).

TABLE 2C

Site 1 Number of Dead Eggs after Shocking

|  | Malachite Green | Bronopol | Negative Control |
|---|---|---|---|
| Original No. of Eggs | 115,520 | 231,040 | 24,320 |
| No. of Dead Eggs After Shocking | 12,960 | 26,201 | 2,417 |

TABLE 2C-continued

Site 1 Number of Dead Eggs after Shocking

|  | Malachite Green | Bronopol | Negative Control |
|---|---|---|---|
| Percentage of Dead Eggs | 11.21% | 11.34% | 9.93% |

TABLE 2D

Site 2 (Batch 1) Number of Dead Eggs after Shocking

|  | Malachite Green | Bronopol | Negative Control |
|---|---|---|---|
| Original No. of Eggs | 13,800 | 16,560 | 5,060 |
| No. of Dead Eggs After Shocking | 650 | 2,000 | 223 |
| Percentage of Dead Eggs | 4.7% | 12.1% | 4.4% |

TABLE 2E

Site 2 (Batch 2) Number of Dead Eggs after Shocking

|  | Malachite Green | Bronopol | Negative Control |
|---|---|---|---|
| Original No. of Eggs | 43,240 | 43,320 | 10,120 |
| No. of Dead Eggs After Shocking | 6,360 | 8,464 | 1,700 |
| Percentage of Dead Eggs | 14.7% | 19.5% | 16.8% |

TABLE 2F

Site 2 (Batch 3) Number of Dead Eggs after Shocking

|  | Malachite Green | Bronopol | Negative Control |
|---|---|---|---|
| Original No. of Eggs | 57,120 | 52,020 | 5,100 |
| No. of Dead Eggs After Shocking | 6,855 | 3,640 | 665 |
| Percentage of Dead Eggs | 12.0% | 7.0% | 13.0% |

TABLE 2G

Number of Dead Eggs after Shocking

|  | Malachite Green | Bronopol | Negative Control |
|---|---|---|---|
| Original No. of Eggs | 45,579 | 249,382 | 24,580 |
| No. of Dead Eggs After Shocking | 5,331 | 52,646 | 4,713 |
| Percentage of Dead Eggs | 11.70% | 21.11% | 19.17% |

TABLE 2H

Site 2 (Batch 1) Number of Dead Eggs after Hatching

|  | Malachite Green | Bronopol | Negative Control |
|---|---|---|---|
| Original No. of Eggs | 13,800 | 16,560 | 5,060 |
| No. of Dead Eggs After Shocking | 1,000 | 2,585 | 477 |
| Percentage of Dead Eggs | 7.2% | 15.6% | 9.4% |

TABLE 2I

Site 2 (Batch 2) Number of Dead Eggs after Hatching

|  | Malachite Green | Bronopol | Negative Control |
|---|---|---|---|
| Original No. of Eggs | 43,240 | 43,320 | 10,120 |
| No. of Dead Eggs After Shocking | 5,900 | 9,450 | 9,600 |
| Percentage of Dead Eggs | 13.6% | 22.3% | 94.9% |

TABLE 2J

Site 2 (Batch 3) Number of Dead Eggs after Hatching

|  | Malachite Green | Bronopol | Negative Control |
|---|---|---|---|
| Original No. of Eggs | 57,120 | 52,020 | 5,100 |
| No. of Dead Eggs After Shocking | 7,300 | 4,200 | 4,100 |
| Percentage of Dead Eggs | 12.8% | 8.1% | 80.4% |

TABLE 2K

Site 3 Number of Dead Eggs after Hatching

|  | Malachite Green | Bronopol | Negative Control |
|---|---|---|---|
| Original No. of Eggs | 45,579 | 249,382 | 24,580 |
| No. of Dead Eggs After Shocking | 8,487 | 47,539 | 7,203 |
| Percentage of Dead Eggs | 18.62% | 19.06% | 36.26% |

TABLE 2L

Summary of Numbers of Dead Eggs after Shocking

|  | Malachite Green | Bronopol | Negative Control |
|---|---|---|---|
| Original No. of Eggs | 275,259 | 592,322 | 69,180 |
| No. of Dead Eggs After Shocking | 32,156 | 92,951 | 9,718 |
| Percentage of Dead Eggs | 11.68% | 15.70% | 14.05% |

TABLE 2M

Summary of Numbers of Dead Eggs after Hatching

|  | Malachite Green | Bronopol | Negative Control |
|---|---|---|---|
| Original No. of Eggs | 159,739 | 360,282 | 44,860 |
| No. of Dead Eggs After Shocking | 22,687 | 63,774 | 21,380 |
| Percentage of Dead Eggs | 14.20% | 17.70% | 47.66% |

Conclusion

Bronopol appears to be as effective as Malachite Green at controlling fungal infections in salmonid eggs. The overall mortalities at hatching for Malachite Green and bronopol are lower than the negative control, with 14.20%, 17.70% and 47.66% dead eggs, respectively.

Trial 3

In Vivo Efficacy of Bronopol Against *Saprolegnia parasitica* Infection in Salmon Method 105 Atlantic salmon (*Salmon salar*) of mixed sex aged approximately 8 months and weighing approximately 30 g on average where divided into three treatment groups, each of 35 fish. Each group was kept in fresh water at 12.5° C. in a 210 litre fibreglass tank. The fish were fed daily with 2% body weight of "Biomar" production feed. After two weeks' acclimatisation, all three groups were artificially infected with *Saprolegnia parasitica*, the date of infection being designated 'day 0' of the trial. The groups were then treated, on days 1, 3 and 5, as follows:

| Groups | Treatment | Treatment concentration | Treatment Duration |
|---|---|---|---|
| 1 | None | — | — |
| 2 | Malachite green | $2 \text{ mg} \cdot \text{l}^{-1}$ | 60 min bath |
| 3 | Bronopol | $30 \text{ mg} \cdot \text{l}^{-1}$ | 15 min bath |

On day 8 of the trial, all fish were culled, and the degree of infection of each fish assessed according to the following scoring system:

| Degree of fungal infection | Score |
|---|---|
| None | 1 |
| Mild (fungus visible on <25% of fish's surface) | 2 |
| Moderate (fungus visible on 50% of fish's surface) | 3 |
| Severe (Lesion(s) on fish) | 4 |
| Mortality* | 5 |

(*Dead fish were removed as mortalities occurred, to avoid contamination of water.)

Results

The number of fish in each category of the above scoring system, and the total score for each group, were as follows:

| SCORE | | CONTROL | Malachite Green | Bronopol |
|---|---|---|---|---|
| None | 1 | 18 | 25 | 23 |
| Mild | 2 | 3 | 1 | 6 |
| Moderate | 3 | 3 | 1 | 2 |
| Severe | 4 | 3 | 0 | 0 |
| Mortality | 5 | 8 | 8 | 4 |
| TOTAL SCORE | | 85 | 70 | 61 |

Figure 4:
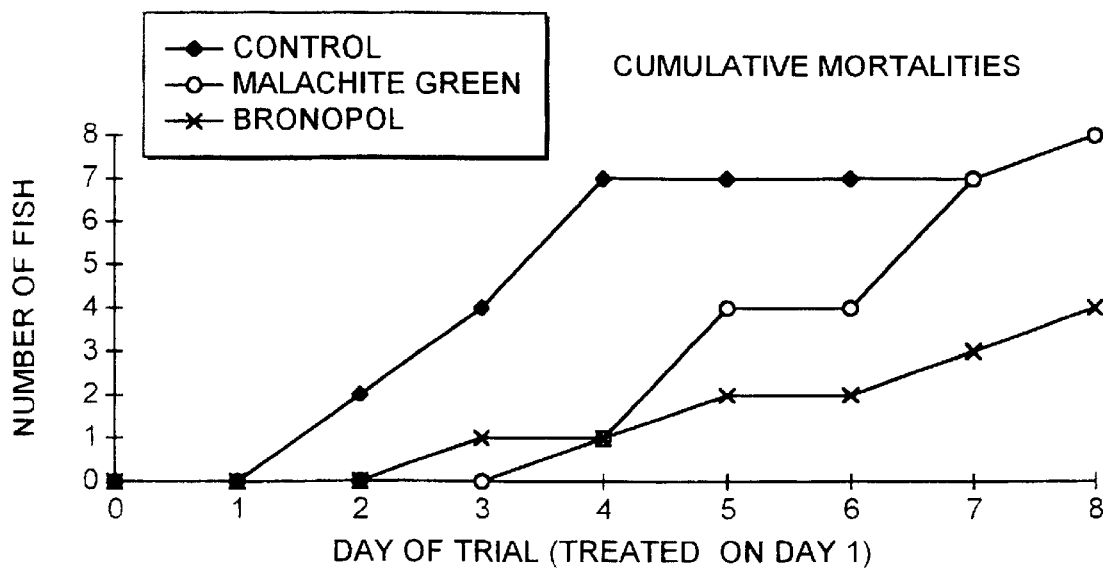
FIG. 4 is a graphical representation of the results of testing conducted to determine the in vivo efficacy of bronopol against *Saprolegnia parasitica* infection in salmon.

The cumulative numbers of mortalities for each day of the trial are illustrated graphically in FIG. 4.

Conclusion

Bronopol proved effective against Saprolegnia infection, and also reduced mortalities by 50% compared to both the non-treatment and the malachite green treatment groups.

Trial 4

In Vivo Efficacy of Bronopol Against *Ichthyobodo necatrix* Infection in Rainbow Trout Method Rainbow trout (*Oncorhyncus mykiss*) having a mean weight of 15 g were used in this trial, and prior to treatment were confined in a single pond with 6 individuals heavily infected with Ichthyobodo. Infection of the previously healthy individuals was confirmed after 5 days by microscopy of mounted gill specimens. Bronopol treatment was administered to a group of 20 fish using the same method as in Trial 3. The Trial was repeated using a group of 19 infected fish treated with formalin (a standard treatment for Ichthyobodo), with a further group of 20 infected fish receiving no treatment and acting as a control. At 7 days after treatment the mean number of parasites per gill filament was assessed in each group (by counting the number of parasites on 10 filaments of each of 5 fish), and at 14 days a further count was conducted, with individual fish being either categorised as having no infection, or being placed in one of four infected categories, according to the degree of infection.

Results

| Days Post Treatment | Infection Level | GROUP | | |
|---|---|---|---|---|
| | | Bronopol | No treatment Control | Formalin |
| 7 | mean numbers of parasites per gill filament | <0.5 | 2.0 | 0 |
| 14 | percentage in each category: | | | |
| | − | 50 | 0 | 100 |
| | + | 43 | 29 | 0 |
| | ++ | 7 | 29 | 0 |
| | +++ | 0 | 18 | 0 |
| | ++++ | 0 | 23 | 0 |

No Mortalities Occurred

Conclusion

Bronopol was shown to have good activity against Ichthyobodo infection in rainbow trout. Although less effective than formalin, its use carries less risk. It may be inferred that bronopol will have similar efficacy against Ichthyobodo infection in other salmonids, and in fish and aquatic organisms in general, and will also be useful in the prophylaxis of the disease.

Trial 5

In Vitro Efficacy of Bronopol Against *Cytophaga psychrophila*

Method

First, the Minimal Bactericidal Concentration (MBC) for bronopol against *Cytophaga psychrophila* was established by growing the organism in broth, and then adding different dilutions of bronopol to establish what concentration would kill the Cytophaga.

Then based on the MBC results, the contact times required to kill the Cytophaga were investigated. A known number of viable bacteria were added to distilled water and exposed to various concentrations of bronopol for 2–40 minutes. Then the bacteria were extracted by filtration, and the extracted bacteria tested for viability by investigating their growth in culture medium by measuring optical density at 520 nm.

Results

Figure 5:
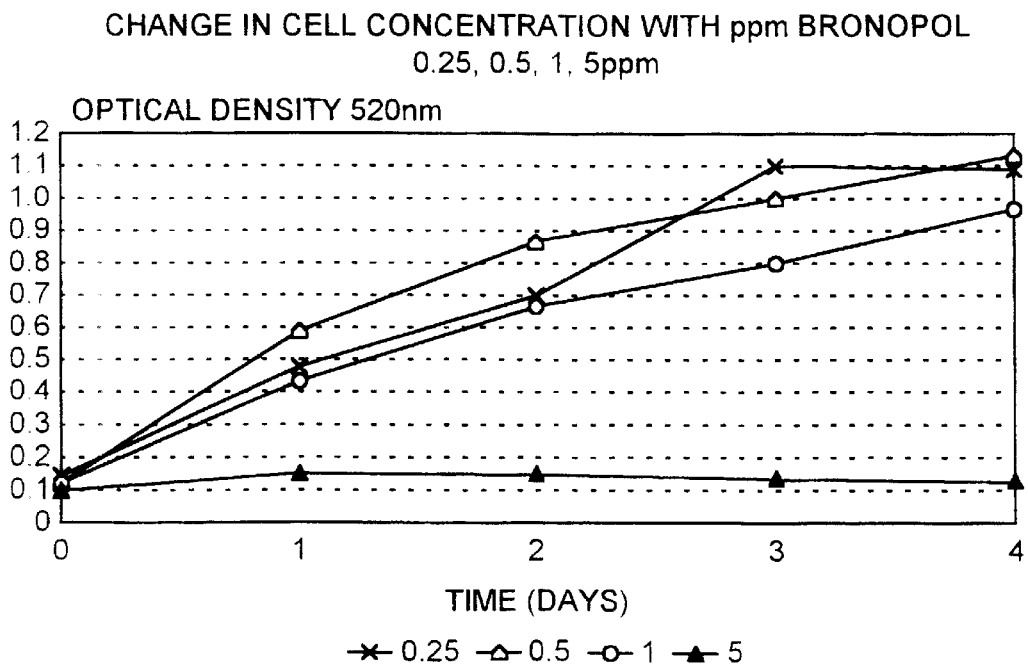
FIG. 5 is a graphical representation of the results of testing conducted to determine the in vitro efficacy of bronopol against *Cytophaga psychrophila*.

The results are set out graphically in FIG. 5. The minimum test concentration which was shown to be effective was 5 mg.l$^{-1}$ (ppm), but it is likely that the actual minimum effective concentration lies between 1 mg.l$^{-1}$ and 5 mg.l$^{-1}$. It was also found that an exposure time of up to 40 mins was required to prevent bacterial growth after re-inoculation onto fresh media when concentrations of between 5 mg.l$^{-1}$ and 400 mg.l$^{-1}$ were used, with the necessary exposure time being reduced to around 4 minutes at a concentration of 1000 mg.l$^{-1}$ and around 2 minutes at 2000 mg.l$^{-1}$.

Conclusion

Bronopol was shown to be active against *Cytophaga psychrophila* at concentrations as low as 5 mg.l$^{-1}$. Cytophaga is an example of the group of bacteria known as myxobacteria, which are characterised by a protective muco-polysaccharide layer, and which are generally resistant to disinfectants (for example, the dose of iodophor disinfectant required to kill Cytophaga is approximately 2000 mg.l$^{-1}$). Based on the known uses of bronopol, this activity is therefore surprising, and may indicate activity against myxobacteria in general. Bronopol is likely to prove a suitable disinfectant treatment for fish tanks and equipment, and may also be of use in the treatment and/or prophylaxis for the various diseases caused by this organism in trout and other salmonids, and also (when these occur) in other fish and aquatic organisms.

Trial 6

In Vivo Efficacy of Bronopol Against *Flavobacterium branchophilum* Infection in Rainbow Trout Seven tanks of 150 rainbow trout each, at a stocking density of 100 g.l$^{-1}$, were included in this experiment. The fish averaged 15 g in size. Water temperature was 11° C. and turned over at a rate of once per hour.

One tank of fish was maintained as a negative control and was neither challenged or treated. An additional tank was challenged, but not treated, to act as a positive control. Two tanks were treated with chloramine-T (a conventional treatment) at a concentration of 10 mgl$^{-1}$. Three tanks were treated with bronopol, one each at the following concentrations: 5, 25 and 50 mg.l$^{-1}$.

Fish were challenged on day 0, and tanks were treated with either chloramine-T or bronopol on days 2 and 4 of the experiment. All six tanks which were experimentally infected with *F. branchiophilum* were treated with the respective therapeutants simultaneously for one hour in a static bath with aeration.

The efficacy of each treatment was evaluated by clinical signs, gill bacterial antigen levels measured by enzyme immunoassay (EIA), mortality rates and cumulative mortality and finally by histological examination.

Gill samples for EIA were collected from five fish in each tank before experimental infection, and before treatment. Further gill samples were collected 6 and 36 hours after the initial treatment, after which the groups were retreated with identical concentrations of the same therapeutant, in an identical manner. Gill samples from five fish from each tank were again collected 6 and 36 hours after the second treatment. Mortality in each tank was recorded each day. The results are presented graphically in FIGS. 6 to 8.

Figure 6:
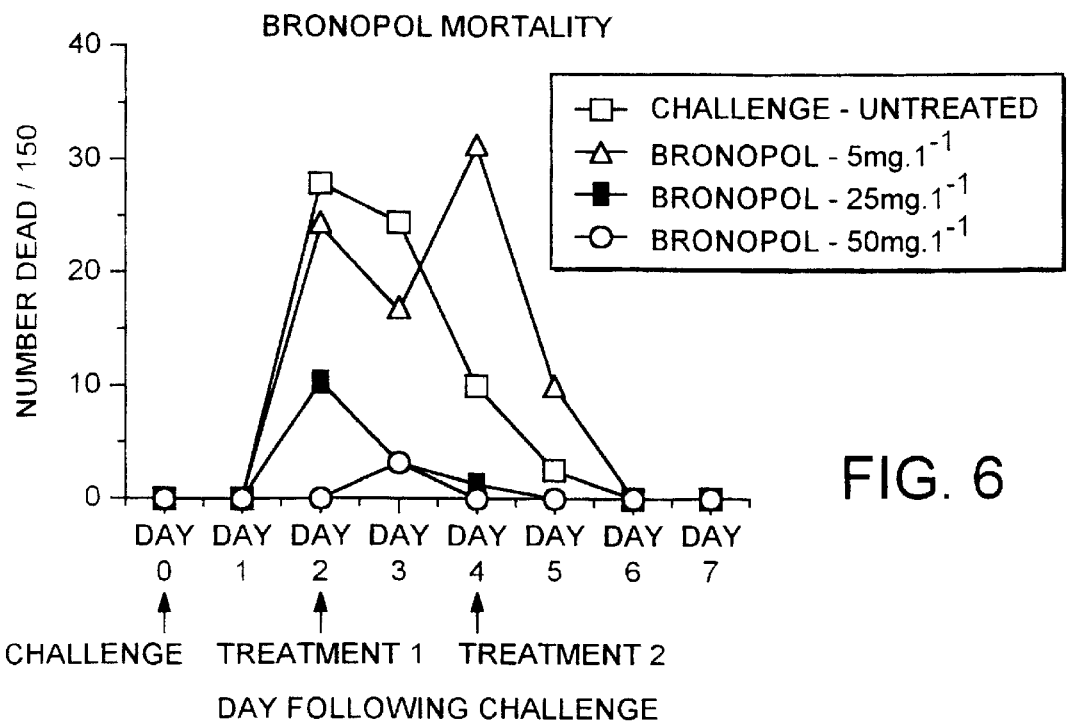
FIGS. 6–8 are graphical representations of the results of testing conducted to determine the in vivo efficacy of bronopol against *Flavobacterium branchophilum* infection in rainbow trout.
Figure 7:
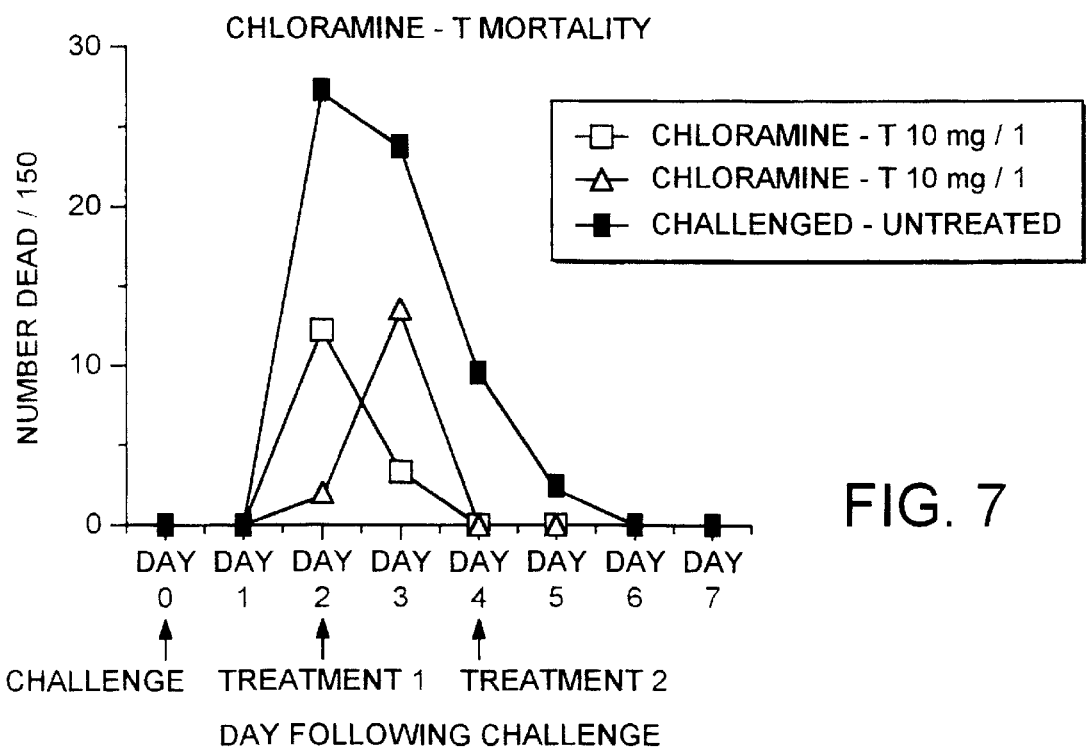

Based on the mortality and EIA data, the lowest concentration of bronopol (5 mg.l$^{-1}$, FIG. 5) was found to be ineffective. Mortality was inversely related to the dose of bronopol (FIG. 6).

Figure 8:
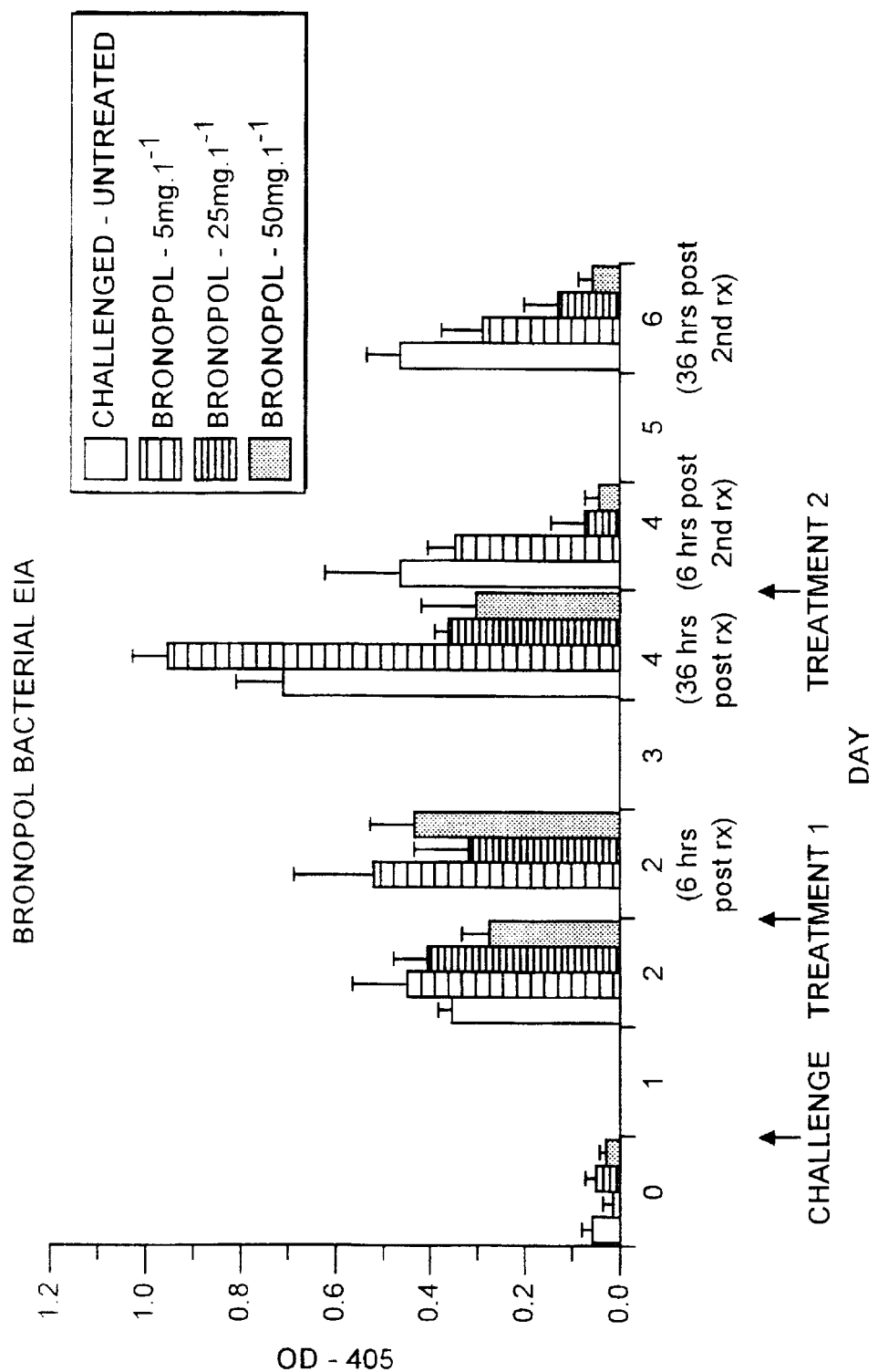

It is evident that mortality corresponds closely with the bacterial antigen levels detected on the gills, and that the EIA is a useful tool for monitoring the efficacy of a therapeutant's ability to eliminate bacteria from the gill surface. As with mortality, the bacterial gill antigen concentration at most sample times, is inversely proportional to the dose of therapeutant (FIG. 8). The two highest concentrations of bronopol effectively eliminated the bacteria from the gill surface after the second treatment (FIG. 8). It is clear that bronopol is effective against *Flavobacterium branchophilum*, and that in the trial bronopol at 25 mg.l$^{-1}$ and 50 mg.l$^{-1}$ reduced mortalities among the infected fish, both compared to the untreated fish, and to the fish treated with chloramine-T.

Trial 7

In Vivo Efficacy of Bronopol Against *Saprolegnia parasitica* in Brown Trout

Method

This trial set out to assess the efficacy of bronopol in the treatment of brown trout naturally infected with *Saprolegnia parasitica*. 40 fish were used in the trial, and these were divided equally into two groups held in separate tanks. A moribund fish heavily infected with *Saprolegnia parasitca* was placed in each tank, with the intention of infecting the other fish naturally. On days 1, 3 and 5 of the trial the fish in one group were treated to a 50 mg.l$^{-1}$ bath of bronopol for 15 min, while the fish in the second group were left untreated and acted as a control. The degree of infection of the fish in both groups was assessed on day 7 of the trial.

Results

In both groups the moribund fish died on day 1 of the trial, but in each case was left in the tank to ensure a good challenge to the remaining fish. On day 7 of the trial all of the fish in the control group were noted to be severely affected by Saprolegnia, and were killed on humanitarian grounds. In contrast, the fish in the bronopol treatment group were all healthy and had no visual signs of Saprolegnia infection.

Conclusion

Repeated treatment with bronopol at a concentration of 50 mg.l$^{-1}$ appears to be highly effective as a treatment for Saprolegnia infection in brown trout, and/or as a prophylactic to prevent infection.

What is claimed is:

1. A method of treatment of an aquatic organism suffering from a disease selected from the group consisting of fungal infections, flagellate protozoan infections, ciliate protozoan infections, bacterial gill disease, and myxobacterial infections, the method comprising the step of administering to said organism, as a topical treatment, a pharmaceutically effective amount of a solution containing, as the sole or principal active ingredient against said disease, a substance selected from the group consisting of bronopol (2-bromo-nitropropane-1,3-diol) and substances which release bronopol when placed in an aquatic environment.

2. A method as claimed in claim 1, for the treatment of a disease caused by a causative organism selected from the group consisting of: *Saprolegnia parasitica, Ichthyobodo necatrix, Icthyophthirius multifiliis, Flavobacterium branchiophilum* and *Cytophaga psychrophila*.

3. The method of claim 2, for the treatment of an organism selected from the group consisting of salmonid fish and salmonid fish eggs.

4. The method of claim 3, wherein the salmonid fish is selected from the group consisting of trout and salmon.

5. The method of claim 1, wherein the concentration of bronopol in the treatment bath is in the range 1 to 1,000 mg.l$^{-1}$ (ppm).

6. The method of claim 5, wherein the concentration of bronopol in the treatment bath is in the range 5 to 200 mg.l$^{-1}$ (ppm).

7. The method of claim 6, wherein the concentration of bronopol in the treatment bath is in the range 10 to 100 mg.l$^{-1}$ (ppm).

8. A method of disinfecting equipment selected from fish tanks and equipment for use in the husbandry of fish, the method comprising the step of exposing said equipment to a solution containing as the sole or principal disinfecting agent a substance selected from the group consisting of bronopol (2-bromo-2-nitropropane-1,3-diol) and substances which release bronopol when placed in aquatic environment.

9. The method of claim 8, wherein the concentration of bronopol is in the range 1 to 2,000 mg.l$^{-1}$ (ppm).

10. The method of claim 9, wherein the concentration of bronopol is in the range 5 to 1,000 mg.l$^{-1}$ (ppm).

11. The method of claim 8, wherein said equipment is exposed to said solution for a period of time in the range 2 to 40 minutes.

12. A treatment bath for the treatment of an aquatic organism suffering from a disease selected from the group consisting of: fungal infections, flagellate protozoan infections, ciliate protozoan infections, bacterial gill disease, and myxobacterial infections, the treatment bath containing as the sole or principal active ingredient against said disease a substance selected from the group consisting of: bronopol and substances which release bronopol when placed in an aquatic environment, at a concentration in the range 1 to 1,000 mg.l$^{-1}$ (ppm).

13. A treatment bath according to claim 12, wherein the concentration of bronopol is in the range 5 to 200 mg.l$^{-1}$ (ppm).

14. A treatment bath according to claim 13, wherein the concentration of bronopol is in the range 10 to 100 mg.l$^{-1}$ (ppm).

* * * * *